United States Patent [19]

Hirayama et al.

[11] Patent Number: 5,279,821
[45] Date of Patent: Jan. 18, 1994

[54] PYROGEN ADSORBENT CONTAINING AMIDE GROUPS

[75] Inventors: Chuichi Hirayama, 373-12, Shimonabe-machi, Kumamoto-shi, Kumamoto-ken; Hirotaka Ihara, 854-2 Takahira, Shimizu-machi, Kumamoto-shi, Kumamoto-ken; Shunsei Tsunoda, Kumamoto; Katsutoshi Aihara, Ueki; Kazufumi Yagyu; Masao Honma, both of Kawasaki, all of Japan

[73] Assignees: Chuichi Hirayama; Hirotaka Ihara, both of Kumamoto; Ajinomoto Co., Inc., Tokyo, all of Japan

[21] Appl. No.: 754,374

[22] Filed: Aug. 30, 1991

Related U.S. Application Data

[63] Continuation of Ser. No. 418,200, Oct. 6, 1989, abandoned.

[30] Foreign Application Priority Data

Oct. 7, 1988 [JP] Japan .................. 63-254342

[51] Int. Cl.⁵ .................. C08G 69/48; C08G 69/08; A61K 37/02; A61K 31/785; A61L 2/16

[52] U.S. Cl. .................. 424/78.17; 424/78.18; 424/491; 424/499; 528/328; 525/54.1; 525/54.11; 525/419; 210/679; 210/692; 210/503; 210/504; 428/364; 428/373; 428/402; 428/403; 526/303.1; 526/936; 514/951; 530/335; 530/345; 530/350

[58] Field of Search .................. 526/303.1; 528/328; 210/679, 692, 635, 654, 198.2, 500.38, 500.37, 500.35, 503, 506; 424/78.17; 525/54.1, 54.11, 419; 530/345, 335, 350

[56] References Cited

U.S. PATENT DOCUMENTS

4,491,660 1/1985 Gendrich .................. 525/303
4,702,840 10/1987 Degen et al. .................. 210/490
4,767,827 8/1988 Iwatsuki et al. .................. 528/328

FOREIGN PATENT DOCUMENTS

0211223 2/1987 European Pat. Off.
2092470 8/1982 United Kingdom.

OTHER PUBLICATIONS

Chemical Abstracts, vol. 101, No. 24, Dec. 1984, Toray Industries, Inc.
Patent Abstracts of Japan, vol. 13, No. 372, Aug. 1989, Chuichi Hirayama.

*Primary Examiner*—Edward Webman
*Attorney, Agent, or Firm*—Oblon, Spivak, McClelland, Maier & Neustadt

[57] ABSTRACT

Here is disclosed a water-insoluble pyrogen adsorbent composed of a polymer possessing amide groups optionally modified, said polymer being, e.g., a poly amino acid, a nylon, on a polyacrylamide.

4 Claims, No Drawings

PYROGEN ADSORBENT CONTAINING AMIDE GROUPS

This application is a continuation of application Ser. No. 07/418,200 filed on Oct. 6, 1989, now abandoned.

BACKGROUND OF THE INVENTION

1. Field of the Invention

This invention relates to a water-insoluble pyrogen adsorbent which is effective in purging medicines, tonics, etc. of pyrogens, i.e., substances which, on entering living bodies in consequence of intravenous administration, e.g., by injection of medicines, tonics, and the like, produce fever.

2. Discussion of the Background

In the production of medicines and the like, for intravenous administration, the technique of purging medicines and the like, of pyrogens has a profound significance.

The term "pyrogens" as used herein refers to those which are classified under exotoxins which are excreted by *Corynebacterium diphtheriae, Staphylococcus aureus*, and the like, and endotoxins which are components of cellular walls of such gram-negative bacteria such as *Escherichia coli*, etc. Of these pyrogens, it is generally those of the latter class, i.e., the endotoxins occurring in the gram-negative bacteria that pose a problem. They have been identified as originating in lipid A, a glycolipid constituting itself the active center in the liposaccharide (LPS), i.e., the composite of lipid with polysaccharide.

It is thought that when a medicine entraining a pyrogen therewith happens to be intravenously administered, e.g., by injection, the pyrogen produces fever by acting on heat centers such as the hypothalamus. The fever may be very serious and at times may bring about death from shock. A manufacturer engaging in the production of a medicine for injection, therefore, is under the obligation to conduct a test with rabbits and confirm safety of the medicine by establishing that the medicine does not entrain any pyrogen with it.

In the existing methods available for the removal of such pyrogens from medicines, and the like, the method which effects the removal by adsorption with carbon powder or ion-exchange resin, the method which attains the removal by decomposing the pyrogen with an acid or an alkali, and the method which accomplishes the removal in a selective manner by the use of an ultramembrane filter, for example, are renowned. A case of successful application of the composite having an imidazole-containing compound such as histamine or a nucleic acid base bonded to a dextran type gel carrier to the adsorptive removal of pyrogens has been reported in literature [Minobe et al: Journal of Chromatography, 262, 193-198 (1983)]. With respect to the conventional methods of the removal of pyrogens from medicines during their production, however, there remains many technical problems to be solved. The medicines themselves to be subjected to the treatment are not stable and the amounts of pyrogens to be removed are extremely small as compared with the amounts of medicines under treatment. With these and other drawbacks as contributory factors, the methods mentioned above have many technical problems yet to be solved for the purpose of effective application to the removal of pyrogens in the production of medicines on a commercial scale. The desirability of developing an effective and expeditious method capable of eliminating all of these problems has been finding growing recognition.

In the circumstances, it has been found that a novel pyrogen adsorbent characterized by using poly amino acid beads as a carrier and having an imidazole derivative deposited fast on the carrier excels in affinity for pyrogens and enjoys advantages in pyrogen adsorption treatment owing to the rigidity of the carrier (Japanese Patent Application Laid-Open (Kokai) HEI 1-127,039 (1989)). The preparation of the pyrogen adsorbent, however, necessitates a process of several steps of reactions and inevitably entails more or less operational intricacies. Moreover, the pyrogen adsorbent has a limited capacity for the incorporation of the imidazole derivative as a ligand and, consequently, a limited capacity for the adsorption of pyrogens.

SUMMARY OF THE INVENTION

An object of this invention is, therefore, to provide a pyrogen adsorbent excellent in the ability of selective adsorption and applicable to the production of medicines, and the like, on a commercial level The present invention is directed to a pyrogen adsorbent which fulfils the object of this invention described above. The characteristics and features of this invention will become apparent from the description to be given further in detail herein below.

To be specific, this invention concerns a water. insoluble pyrogen adsorbent which is formed of a polymer possessing amide groups, and which may optionally contain solely a modifying group having an aliphatic group and/or an aryl group in the side chain and/or at the terminal of the main chain thereof The term "polymer" as used herein refers to the polymer of one member selected from among amide group-containing poly amino acids, nylons, and polyacrylamides, for example.

DETAILED DESCRIPTION OF THE INVENTION

In view of the problems mentioned above, the inventors have further continued a diligent study to find that a water-insoluble substance which is formed of a polymer possessing amide groups and which may optionally contain solely a modifying group having an aliphatic group and/or an aryl group in the side chain and/or at the terminal of the main chain thereof exhibits extremely high affinity for pyrogens and possesses a remarkable ability to effect adsorptive removal of pyrogens from medicinal substances, and the like, intended for intravenous administration, e.g., by injection. This invention has been accomplished as the result.

The pyrogen adsorbent of this invention is characterized by a water-insoluble substance which is formed of a polymer possessing amide groups and may optionally contain solely a modifying group having an aliphatic group and/or an aryl group in the side chain and/or at the terminal of the main chain thereof.

Various known methods have, as has been described, been tried for the removal of pyrogens In the operation for the removal of pyrogens from medicines in pharmaceutical production, more often than not the selective removal of pyrogens by adsorption is not attained fully as expected because of the problem that the amount of pyrogens to be removed is very small as compared with the relatively high concentration of the medicinal substance in the material under treatment. Thus, the desirability of developing an absorbent possessing highly selective affinity for pyrogens and a method of removing pyrogens in high efficiency has been finding enthusiastic recognition. Further, the method for the removal of pyrogens as one step in pharmaceutical production is expected to feature quickness of treatment in addition to the selective affinity mentioned above.

The pyrogen adsorbent of this invention exhibits prominent affinity for pyrogens owing to the use of an amide group-containing polymer in place of agarose gel or dextran type cephalose gel which has found utility in the conventional technique for adsorbents. Further, the pyrogen adsorbent of this invention possesses an ability to effect efficient and quick separation and removal of pyrogens from a medicinal substance under treatment for purification owing to the characteristic of its high rigidity as compared with the rigidity of the conventional polysaccharide gel.

The aliphatic group-containing modifying groups which are usable for the pyrogen adsorbent of this invention include alkyl groups represented by methyl group and cyclohexyl group, allyl groups such as vinyl group, ether groups such as methoxy group, carboxyl group, ester groups represented by ethoxycarbonyl group, acyl groups such as acetyl group and cyclohexylcarbonyl group, alkylamino groups such as methylamino group and aminoethylamino group, carbamoyl group, and mesyl group, for example.

The aryl group-containing modifying groups include aryl groups such as phenyl group, aralkyl groups such as benzyl group, ether groups such as phenoxy group and benzyloxy group, ester groups represented by benzyloxycarbonyl group, acyl groups such as benzoyl group, amino groups such as benzylamino group which are linked to aromatic compounds through the medium of an aliphatic spacer, and toluenesulfonyl group, for example.

The amide group-containing polymers which are usable for the pyrogen adsorbent of the present invention include poly amide acids which are polymers of amino acids, nylons composed of diamines and dibasic acids, and polyacrylamides which are polymers of acrylic acid amides, for example.

More specifically, the poly amide acids embrace inherently hydrophobic amino acid polymers composed of neutral amino acids such as alanine, phenylalanine, valine, and leucine, for example.

In addition, hydrophilic poly amino acids which have been rendered hydrophobic (i.e. hydrophilic amino acid polymers having incorporated therein a hydrophobic group) are also usable and within the concept of "amide group-containing polymer". The hydrophilic poly amide acid derivatives which answer the foregoing description include those obtained by hydrophobically esterifying the free carboxyl groups of acidic poly amino acids such as poly glutamic acids and poly amide acids, specifically represented by alkyl esters, benzyl esters, dicyclohexanemethyl esters, and tetrahydropyran methanol esters of such poly acids. Besides, those obtained by protecting basic amino acids such as lysine and ornithine with a hydrophobic group, specifically represented by carbobenzoxylated products and carboethoxylated products of such amino acids, are other examples, and are within the concept of "amide group . containing polymer".

The poly amino acid to be used in the present invention may be either a homopolymer of one amino acid or a copolymer of two or more amino acids Those obtained by acylating the terminal amino group of the poly amino acids mentioned above, specifically represented by acetylated products and benzoylated products of poly amino acids, are other examples and are within the concept of "amino group-containing polymer" and those obtained by the reaction of poly amino acids with an isocyanate compound, specifically represented by the incorporation of carbamide in poly acids are further examples within that concept.

Copolymers of a poly amino acid or a poly amino acid derivative with a urethane prepolymer or an epoxy resin are also usable and are within that concept.

Poly amino acid derivatives which are not suitable for the pyrogen adsorbent of this invention include those poly glutamic acid derivatives obtained by modifying with glutaric acid such poly glutamic acids having the side chains thereof amidated with ethylene diamine.

The pyrogen adsorbent of this invention is enabled to acquire enhanced adsorptive activity due to a basic functional group carried by the poly amino acids or poly amino acid derivatives. The poly amino acid derivatives rendered hydrophobic, e.g., by esterification, specifically represented by poly glutamic acid methyl ester, are allowed to acquire a further addition to the ability of pyrogen adsorption by having the ester moiety thereof aminated, and the hydrophobic derivatives of lysine, ornithine and the like, inherently having an amino group in the side chains thereof, specifically represented by poly($N^\epsilon$-carbobenzoxylysine), are allowed to acquire an enhanced ability for pyrogen adsorption by eliminating the hydrophobic group in the manner conventionally practised in the art.

The term "basic functional group" as used herein refers preferably to an amino group, especially an aliphatic amino group. In greater detail, alkyl amines represented by ethyl amine, aliphatic amines such as ethylene diamine, diethylene diamine, and benzyl amine, and amines linked to aromatic compounds through the medium of a spacer are usable and within the purviews of this invention. Substantially all of the basic functional groups which are usable in the present invention possess acid ionization indexes, pKa, of not less than 6.5. The incorporation of these basic functional groups into the aforementioned poly amino acid or poly amino acid derivative is accomplished either directly or indirectly through the medium of a spacer.

By effecting the incorporation through the medium of a spacer, the adsorbent of this invention can be produced with outstanding affinity for pyrogens. The spacer thus used must be selected so as to suit the poly amino acid or poly amino acid derivative of which the adsorbent of this invention is to be formed. In the case of poly amino acid derivatives, including a glutamic acid derivative or an aspartic acid derivative, for example, a polyamine having two to six carbon atoms is advantageously used as the spacer.

For the incorporation under discussion, the number of basic functional groups to be incorporated is not critical.

The poly amino acids or polyamino acid derivatives to be used for the pyrogen adsorbent of the present invention are not specifically limited. However, in consideration of the ease with which the raw material is procured, i.e., the ease of synthesis, and the ease of chemical modification to be made subsequently to the preparation of adsorbent beads, it is desirable to use, e.g., a poly glutamic acid ester, a poly aspartic acid ester, or a hetero-polymer partly composed of a glutamic acid ester or an aspartic acid ester and mainly of other hydrophobic amino acid, or polylysine or polyornithine both rendered hydrophobic, or a heteropolymer partly composed of hydrophobic polylysine or hydrophobic polyornithine and mainly of other hydrophobic amino acid. In the preparation of the adsorbent of this invention which is composed of a glutamic acid derivative and/or an aspartic acid derivative, for example, the poly amino acid derivative aimed at can be produced by using a methyl ester, an ethyl ester, a propyl ester, or a benzyl ester of the relevant amino acid as the new material.

Though the polymerization degree of the poly amino acid or poly amino acid derivative is not specifically restricted, it is desired to exceed 100, preferably to fall in the range of 100 to 1,000, from the viewpoint of the strength of the pyrogen adsorbent.

The nylons which are usable in the present invention include 6.nylon, 6,6-nylon, 6,10-nylon, 6,12-nylon, 11-nylon, and 12-nylon, for example. In consideration of the ease of procurement of raw material and the ease of synthesis, it is advantageous to use 6-nylon, 6,6-nylon, or 12-nylon. A mixture of two or more of these nylon species or a copolymer thereof may be used.

The preparation of the nylons can be easily accomplished by thermal polymerization or interfacial polycondensation as practised in the art.

The polyacrylamide derivatives include a polymer which is obtained by copolymerizing acrylamide or methacrylamide with N,N'-methylenebisacrylamide. The resultant copolymer is insoluble in water. From the viewpoint of the strength, the content of N,N'-methylenebisacrylamide in this polymer is desired to exceed 50%.

The preparation of the polyacrylamide derivative is easily carried out by photopolymerization or radical polymerization as practised in the art.

The shape of the pyrogen adsorbent of this invention is not specifically restricted. The adsorbent may be spherical particles, fibers, film, or powder, for example. Particularly, the spherical particles, i.e. one of the forms in which the pyrogen adsorbent of this invention is put to use, are made of a poly amino acid (synthetic polyamino acid) or a nylon, which is totally different material from the polysaccharide type materials used in the conventional adsorbent in the form of spherical particles. The present inventors have already invented basic spherical particles of such a poly amino acid as described above and a process for the production thereof and filed a patent application on these inventions in Japan (Japanese Patent Application Laid-Open (Kokai) SHO 62-1,728(1987)).

In the preparation of the spherical particles of poly amino acid as the pyrogen adsorbent of the present invention, these spherical particles can be obtained by using an inherently hydrophobic poly amino acid or a poly amino acid derivative rendered hydrophobic as a raw material.

To be specific, the spherical particles are formed by dissolving either a hydrophobic poly amino acid or a poly amino acid derivative rendered hydrophobic in an organic solvent, adding the resultant solution to an aqueous medium (in which said resultant solution does not dissolve or is sparingly soluble), causing the added solution to be suspended in the aqueous medium, and expelling the organic solvent from the resultant suspension. The spherical particles may be further modified as occasion demands.

Only so long as the spherical particles mentioned above are allowed to assume the form of a hydrophobic poly amino acid derivative particularly during the step for preparation of a dispersion, the spherical particles of a hydrophobic poly amino acid derivative and a hydrophilic poly amino acid derivative inclusive of an amphipatic poly amino acid derivative can be finally obtained by eliminating the protective group after the formation of spherical particles.

The selection from among the hydrophobic and the hydrophilic poly amino acid derivative particles to be prepared hinges heavily on the quality of the medicinal substance, and the like, from which pyrogens are to be removed. Generally, when a medicinal substance to be treated for purification is hydrophilic, for example, both the hydrophilic and hydrophobic poly amino acid derivative particles can be invariably effectively used without any particular restriction. On the other hand, when a medicinal substance happens to be hydrophobic, however, the hydrophilic poly amino acid derivative particles are employed more advantageously.

Among organic solvents to be used in the preparation of the spherical particles of poly amino acid as the pyrogen adsorbent of this invention, those which dissolve the hydrophobic polyamino acid or poly amino acid derivative satisfactorily, exhibit no solubility in water, and possess a lower boiling point than an aqueous medium solvent, are most preferred. The organic solvents which prove to be advantageous for use herein include chloroform, dichloromethane, dichloroethane, other similar halogenated hydrocarbons, benzene, and mixtures thereof. In the preparation of this nature, the solution obtained by polymerizing an amino acid or an amino acid derivative in an organic solvent thereby producing a hydrophobic poly amino acid or poly amino acid derivative can be used in its unmodified form.

The diameter of the spherical particles can be easily controlled by the viscosity of the organic solvent-aqueous medium system and the stirring speed. Generally, the diameter of the produced spherical particles increases in proportion as the concentration of the poly amino acid or polyamino acid derivative in the organic solvent increases and the viscosity of the aqueous medium system decreases. The spherical particles can be obtained in a small diameter by increasing the stirring speed. The control of the diameter of the spherical particles can be further facilitated by the addition of a viscosity regulator such as partially acetified polyvinyl alcohol or gelatin.

The particle diameter is not critical, but usually selected from the range of 5–300 μm.

The spherical particles can be easily prepared with a porous texture. Specifically, this preparation is accomplished by following the procedure of the preparation of the spherical particles described above, excepting that an additive exhibiting incompatibility with the hydrophobic polyamino acid or the polyamino acid derivative rendered hydrophobic and compatibility with the organic solvent having dissolved the polyamino acid or polyamino acid derivative and possessing a higher boiling point than the organic solvent or an aqueous medium is added to the solution of the hydrophobic polyamino acid or polyamino acid derivative rendered hydrophobic in the organic solvent The additives which answer this description include decalin, tetralin, toluene, xylene, ethylbenzene, diethylbenzene, anisole, hexanol, octanol, dibutyl ether, cyclohexane, paraffins, phthalic acid esters such as dibutyl phthalate, higher fatty acid esters such as methyl dodecanoate, and higher saturated fatty acids such as oleic acid, for example. By selecting the kind of the additive and adjusting the amount of the additive to be used, the porous spherical particles can be obtained with a pore diameter in the range of $10^2$ to $10^7$ as expressed in the molecular weight of water-soluble polysaccharide and a porosity in the range of 10 to 99%. To be particularly desirable for this invention, the spherical particles possess a porosity in the range of $10^3$ to $10^7$. When these spherical particles are prepared by the method described above, they can be produced with a freely controlled diameter. Generally, the spherical particles obtained by this method acquire a diameter in the range of 1 to 300 $\mu$m. However, by adjusting the viscosity of the reaction solution or the stirring speed, the diameter of the spherical particles can be adjusted in the range of 0.1 to 1 mm. The particle size is selected so as to suit the particular use to which the produced spherical particles are put. When the spherical particles are intended for use in column chromatography, for example, the spherical particles having a diameter in the range of 5 to 300 $\mu$m prove to be advantageous.

The spherical particles of the quality described above are characterized by the fact that they are rigid as compared with the polysaccharide type spherical particles in popular use to date. An analysis of the infrared absorption spectrum of these spherical particles revealed the presence of the $\beta$ structure at least partly. It is believed that the presence of the $\beta$ structure contributes in a large measure to the rigidity of the spherical particles.

The preparation of the pyrogen adsorbent in the form of fibers is carried out easily by the conventional method. Specifically, the fibers of pyrogen adsorbent are obtained by preparing a solution of a polyamino acid or polyamino acid derivative in an organic solvent and extruding this solution into an organic solvent which is incompatible with the poly amino acid or poly amino acid derivative. The diameter of these fibers is suitably selected by the diameter of the spinning nozzle to be used for the spinning. Generally, the fibers 30 to 60 $\mu$m in diameter are actually put to use.

The fibers of a nylon are prepared by melt spinning.

The diameter of the fibers is not critical, but usually in the range of 30-60 $\mu$m.

The preparation of the pyrogen adsorbent in the form of film can be easily carried out by the conventional method. Specifically, the film of pyrogen adsorbent can be obtained, e.g., by preparing a solution of a poly amino acid or poly amino acid derivative in an organic solvent, casting the solution on a glass plate, and expelling the organic solvent from the cast sheet of the solution. The thickness of this film is suitably selected at the time that the solution is cast on the glass sheet. The nylon film or the film of a polyacrylamide derivative is prepared by the method of melt extrusion.

The thickness of films is not critical, but usually in the range of 10-50 $\mu$m.

The preparation of the pyrogen adsorbent in the forms of powder is carried out by any of the various methods described herein below, for example. The powder of a poly amino acid or poly amino acid derivative can be easily prepared by heterogeneous polymerization. Specifically, the powder can be obtained by polymerizing an amino acid or amino acid derivative in an organic solvent compatible with an amino acid N-carboxy anhydride, a polymerizable monomer, and incompatible with the poly amino acid to be subsequently produced thereby inducing precipitation of a corresponding poly amino acid or poly amino acid derivative, and separating the precipitate. The preparation of the nylon powder is effected by the method which comprises melting the nylon at an elevated temperature in an organic solvent compatible with the nylon at the elevated temperature and incompatible with the nylon at normal room temperature and cooling the resultant hot solution thereby allowing the suspended nylon particles to settle or by the method of mechanical pulverization. The powder of a polyacrylamide derivative can be easily obtained by photopolymerization.

The size of powder is not critical, but usually in the range of 5-300 $\mu$m.

The product obtained by treating the surface of a porous carrier of silica or alumina with a poly amino acid or poly amino acid derivative, nylon, or a polyacrylamide derivative can be used The porous carrier having the surface thereof treated with a poly amino acid or poly amino acid derivative can be easily obtained by dispersing a porous carrier in the solution of the poly amino acid or poly amino acid derivative in an organic solvent, then separating the impregnated carrier from the dispersion, and drying the separated carrier. The porous carrier to be used in this case is not specifically restricted. The inorganic carrier of silica or alumina which has a large specific surface area can be advantageously used. The fibers formed of a material such as cellulose, polyester, polyacrylonitrile, a polyolefin and the like, and having the surface thereof coated with a poly aminoacid or poly amino acid derivative are also usable. Though the fibers thus used have no particular restriction, the ease with which they are put to use increases in proportion as their specific surface area increases.

The porous carrier and the fibers which have their surfaces coated with a poly amino acid or poly amino acid derivative, nylon, or a polyacrylamide derivative are characterized by the fact that, similarly to the spherical particles, they possess high rigidity and a large specific surface area as compared with the conventional spherical particles of polysaccharide type. Thus, they are capable of efficiently and quickly removing pyrogens from a finally refined medicinal substance. Further, they are economically advantageous over the spehrical particles in the sense that they need the polymer in a small application ratio.

The removal of pyrogens by the use of the pyrogen adsorbent described above can be executed by either column chromatography or batchwise treatment. In the method of column chromatography, the medicinal substance freed of pyrogens can be obtained by filling a column with the pyrogen adsorbent of this invention, washing the packed column with a suitable buffer, then passing a pyrogen-containing solution of the medicinal substance through the packed column, and collecting the fraction flowing out of the column In the method of batchwise treatment, the medicinal substance freed of pyrogens can be obtained by stirring the pyrogen adsorbent of this invention in a pyrogen-containing solution of the medicinal substance and then removing the adsorbent from the resultant mixture.

The pyrogen adsorbent of the present invention exhibits virtually no swelling property and allows the treatment of column chromatography to be quickly carried out thereon as compared with the conventional adsorbent particles of agarose or dextrin. Thus, it functions optimally when it is used as a quick pyrogen-removing agent in the commercial production of a medicinal substance and the like.

The pyrogen adsorbent of this invention possesses excellent affinity for pyrogens and, at the same time, abounds in rigidity and consequently in stability and exhibits an extremely small swelling degree as compared with the conventional adsorbent particles using an agarose or dextran type substance and, therefore, allows the operation for removal of pyrogens to be carried out quickly thereon.

Moreover, the pyrogen adsorbent of this invention can be prepared very simply and conveniently without involving any special reaction path. Further, since the pyrogen adsorbent of this invention possesses low affinity for the medicinal substance subjected to purification, it is capable of removing pyrogens with extremely high selectivity without a sacrifice of the recovery rate of the finally refined medicinal substance.

The feature of the pyrogen adsorbent of this invention, i.e. the optimum function the adsorbent fulfils in the adsorption of pyrogens as demonstrated above, may be safely ascribed to the synergism between the effect the amide group-containing polymer's structure produces on the mechanism of adsorption of pyrogens and the affinity the introduced basic functional group, particularly the weakly basic amino group, manifests for the pyrogens. It is also noteworthy that in the introduction of the basic functional group, the particular kind of the group can be suitably selected and the ratio of the introduction can be easily controlled.

EXAMPLES

Now, the present invention will be described more specifically below with reference to working examples.

Preparation of Pyrogen Adsorbent

Example 1

A solution of 10 g of poly methyl-L-glutamate and 10 ml of decalin in 400 ml of dichloroethane was added dropwise to 2,000 ml of an aqueous 1.5 w/v % partially acetylized polyvinyl alcohol kept at 50° C. When the resultant mixture was vigorously stirred at the same temperature for 24 hours, dichloroethane was expelled by vaporization and spherical particles of decalin-containing poly methyl-L-glutamate were obtained.

The spherical particles were washed to be freed of decalin by the method of Soxhlet extraction using acetone, suspended in water, and passed through standard sieves of Japanese Industrial Standard (JIS) to obtain spherical particles of diameters in the range of 64 to 105 µm. These spherical particles had the maximum pore diameter of $2 \times 10^4$ as expressed in the molecular weight of water-soluble polysacchride and a porosity of 55%.

The particles thus obtained were labeled as "Adsorbent A (PG-OMe)".

Example 2

In a mixed solution consisting of 50 ml of methanol and 50 ml of ethylene diamine, 5 g of Absorbent A obtained in Example 1 was suspended and then stirred gently at 65° C. for 48 hours The particles were collected by filtration and then washed with methanol and water, to obtain amino group-introduced particles.

The amount of amino groups introduced in the particles was determined by the ion electrode method to be 3.2 meq/g (3.2 milliequivalents per 1 g of the particles).

The particles thus obtained were labeled as "Adsorbent B (PG-NH$_2$)".

Comparative Experiment 1

In 100 ml of tetrahydrofuran, 4 g of Adsorbent B obtained in Example 2 was suspended and 0.14 g of glutaric anhydride was added thereto. The resultant mixture was gently stirred at 40° C. for 24 hours. The particles which were consequently produced in the mixture were collected by filtration and then washed with methanol and water, to obtain carboxyl group-introduced particles. By the method of titration, it was confirmed that not less than 98% of the amino groups in the particles had been carboxylated.

The particles thus obtained were labeled as "Adsorbent C (PG-COOH)".

Comparative Experiment 2

In 50 ml of water, 3.5 g of Adsorbent C obtained in Comparative Experiment 1 and 3 g of histamine dihydrochloride were suspended and then slowly stirred in conjunction with 4.5 ml of triethyl amine and 0.56 g of a water-soluble carbodiimide [such as, for example, 1-cyclohexyl-3-(2-morpholinoethyl)-carbodiimide-p-toluenesulfonate] at room temperature for two days. The particles consequently formed in the stirred mixture were collected by filtration and then washed sequentially with water, alcohol, and ether.

By the method of amino acid analysis, the histamine content of the particles was found to be 0.2 meq/g.

The particles thus obtained were labeled as "Adsorbent D (PG-His)".

Example 3

At room temperature, 10 g of poly-L-leucine and 10 ml of diethylbenzene and 500 ml of benzene were stirred for several hours to swell the polymer and then were heated to 70° C., to give rise to a viscous transparent solution. This solution was added dropwise to 2,000 ml of an aqueous 2.5 w/v % partially acetylized polyvinyl alcohol solution The resultant mixture was vigorously stirred for 24 hours with the temperature of the system gradually being lowered to 40° C. Consequently, benzene was expelled by vaporization and spherical particles of diethylbenzene-containing polyleucine were obtained.

The spherical particles were washed to be freed of diethyl-benzene by the method of Soxhlet extraction using acetone and then passed through standard sieves of JIS. Consequently, there were obtained spherical particles of diameters in the range of 10 to 25 µm.

The particles thus obtained were labeled as "Adsorbent E (PLeu)".

Example 4

A solution of 10 g of poly(N$^\epsilon$-carbobenzoxy-L-lysine) in 10 ml of diethylbenzene and 400 ml of chloroform was added dropwise to 2,000 ml of an aqueous 1.5 w/v % partially acetylized polyvinyl alcohol solution kept at 40° C. When the resultant mixture was vigorously stirred at the same temperature for 24 hours, the chloroform was expelled by vaporization and spherical particles of diethylbenzene-containing poly(N$^\epsilon$-carbobenzoxy-L-lysine) were obtained.

The spherical particles were washed to be freed of diethylbenzene by the method of Soxhlet extraction using acetone and then passed through standard sieves of JIS, to produce spherical particles of diameters in the range of 64 to 105 μm. To 10 g of the spherical particles were added 30 ml of 25% hydrogen bromide/acetic acid and 300 ml of ether, and the mixture was stirred at room temperature for one hour, there were obtained poly-L-lysine particles partially freed of carbobenzoxy groups.

The particles thus obtained were labeled as "Adsorbent F (PLys)".

Example 5

A solution of 1.0 g of L-leucine-N-carboxylic anhydride and 0.2 g of L-isoleucine-N-carboxylic anhydride in 15 ml of acetonitrile was heated to 40° C. The solution, on addition thereto of 4 μl of triethyl amine, began to form a powdery polymer.

On elapse of six hours thereafter, the system was cooled to room temperature to induce precipitation of the powdery polymer. The polymer was separated by filtration and dried Consequently, 0.9 g of poly(L-leucyl-L-isoleucine) was obtained.

The particles thus obtained were labeled as "Adsorbent G (PLeu-Ile)".

Example 6

A 10 wt % solution poly methyl-L-glutamate in dichloroethane was heated to a temperature in the range of 40° to 50° C. and deaerated under vacuum.

The spinning dope consequently obtained was placed in a spinning syringe and discharged from the syringe at a fixed rate into kerosene. Fibers were obtained by drawing the poly methyl-L-glutamate coagulated at the leading end part of the nozzle of the syringe into a coagulation bath and taking up the coagulated thread on a bobbin kept in rotation at a fixed rate.

The fiber thus obtained was labeled as "Adsorbent H (Fibrous PG-OME)".

Example 7

A solution of 1.4 g of L-glutamic acid methyl-N-carboxy anhydride in 10 ml of ethyl acetate was heated to 40° C. The solution, on addition thereto of 5 μl of triethyl amine, began to educe poly methyl-L-glutamate. On elapse of four hours thereater, the system was cooled to room temperature to induce precipitation of the poly methyl-L-glutamate. The polymer was separated by filtration and then dried. Consequently, there was obtained 1 g of poly methyl-L-glutamate.

The particles thus obtained were labeled as "Adsorbent I (Powder PG-OME)."

Example 8

A solution of 1 g of poly methyl-L-glutamate in 100 ml of dichloroethane was stirred gently with 1 g of porous silica (particle diameters of 0.5 to 11 μm) at room temperature for two hours. The resultant mixture was deaerated under vacuum for 5 minutes, to displace the interior of the porous silica with the polymer solution. The procedure just described was repeated twice. Then, the porous silica was separated by filtration, washed with methanol, and then dried. Consequently, there was obtained 1 g of porous silica having the surface thereof treated with poly methyl-L-glutamate.

The particles thus obtained were labeled as "Adsorbent J (surface-treated PG-OME)".

Example 9

In a mixed solvent consisting of 4 ml of water and 1 ml of ethanol, 0.5 g of acrylamide and 0.5 g of N,N'-methylenebisacrylamide were dissolved. To the resultant solution, 10 mg of benzophenone-2,4'-dicarboxylic acid was added. The solution thus obtained was deaerated under vacuum for about 15 minutes and then spread in a thickness of 1 to 2 mm on the bottom of a petri dish.

The layer of the solution, on exposure to the ultraviolet light from a high-pressure mercury-vapor lamp for 5 minutes, turned into a white solid film. This solid film was removed from the petri dish and crushed. Consequently, 0.9 g of polyacrylamide was obtained. The particles thus obtained were labeled as "Adsorbent K (Paa)".

Adsorptive Removal of Pyrogens

Example 10

Samples, 0.1 to 0.2 g (dry weight), of the adsorbents prepared in Examples 1 to 4 and Comparative Experiments 1 and 2 and two commercially available adsorbents (produced by A company and B company) were each washed sequentially with a 10 mM pyrogen-free phosphate buffer of pH 7.5 (containing 1.0 M NaCl) and a 10 mM pyrogen-free phosphate buffer of pH 7.5 (containing 0.07 M NaCl). The respective washed samples were brought into contact with 1 to 2 ml of various bacterial toxoid solutions containing pyrogens The eluates or supernatants consequently formed were tested for pyrogen content.

The ratio of adsorption was found by subtracting the amount of pyrogen remaining in the eluates or supernatants from the amount of pyrogen contained initially in the bacterial toxoid solutions, dividing the difference by the amount of pyrogen contained initially in the bacterial toxoid solutions, and multiplying the resultant quotient by 100. The results were as shown in Table 1.

From the results, it is clearly noted that Adsorbent A itself possessed a fairly distinct ability to adsorb pyrogens and Adsorbent B having weakly basic amino groups introduced into the side chain thereof through the medium of a spacer exhibited a further enhanced ability to adsorb pyrogens.

In contrast, Adsorbent C having carboxyl groups introduced in the side chain thereof showed virtually no ability to adsorb pyrogens, indicating that the carboxyl groups suppressed the ability to adsorb pyrogens.

Adsorbent D having imidazole derivatives (histamine) introduced in the side chain of Adsorbent C exhibited a pyrogen-adsorbing ability equivalent to the ability of the Adsorbent A with respect to toxoid C but not comparable with the ability of Adsorbent B with respect to any of the toxoids in Table 1. When Absorbent of A company using chitosan as the main body of adsorbent and Adsorbent of B company using cephalose as the carrier and having imidazole linked thereto through the medium of a spacer were used, their effects determined by the method employed herein were not insignificant but were not fully satisfactory as expected.

Adsorbent E using polyleucine, a hydrophobic poly amino acid, as the main body of adsorbent and Adsorbent F inherently possessing amino groups in the side chain thereof each showed an appreciable pyrogen-adsorbing ability, supporting the practical utility of the present invention.

TABLE 1

| | | Adsorbent's capacity for adsorptive removal of pyrogens | | |
|---|---|---|---|---|
| | | Ratio of adsorption (%) | | |
| Pyrogen adsorbent (g) | | Concentrated crude toxoid A (originating in Chlostridium titani); pyrogen concentration 3,933 ng/ml | Concentrated crude toxoid B (originating in Chlostridium titani); pyrogen concentration 1,080 ng/ml | Concentrated crude toxoid C (originating in Diphtheria); pyrogen concentration 397 ng/ml |
| This invention | | | | |
| Adsorbent A (PG-OMe) | 0.194 | 81 | 86 | 68 |
| Adosrbent B (PG-NN$_2$) | 0.185 | 95 | 100 | 100 |
| Adsorbent E (Pleu) | 0.156 | 78 | 83 | 86 |
| Adsorbent F (PLys) | 0.168 | 86 | 92 | 98 |
| Comparison | | | | |
| Adsorbent C (PG-COOH) | 0.115 | 0 | 0 | — |
| Adsorbent D (PG-His) | 0.101 | 0 | 16 | 91 |
| Adsorbent of A company | 0.200 | 0 | 0 | 72 |
| Adsorbent of B company | 0.124 | 20 | 4 | 54 |

Example 11

A mixture of 0.05 g (dry weight) of Adsorbent A prepared in Example 1 and 0.05 g (dry weight) of Adsorbent E prepared in Example 3 was treated by following the procedure of Example 10 and tested for the residual pyrogen content. The ratio of adsorption was found in the same manner as in Example 10.

As the result, the ratio of adsorption of pyrogen was found to be 81%. This value was practically equal to the values found for Adsorbents A and B under the conditions mentioned above.

Example 12

Samples, 0.1 g (dry weight), of the adsorbents prepared in Examples 5 to 8 were each washed sequentially with a 10 mM pyrogen-free phosphate buffer of pH 7.5 (containing 1.0 M NaCl) and a 10 mM pyrogen-free phosphate buffer of pH 7.5 (containing 0.07 M NaCl).

The washed samples were each brought into contact with 1 to 2 ml of a phosphate buffer (pH 7.2) having 200 to 250 ng of pyrogens originating in varying bacteria. The eluates or supernatants consequently formed were tested for the residual pyrogen content.

The ratio of adsorption was determined in the same manner as in Example 10.

The results are as shown in Table 2. These adsorbents invariably exhibited highly satisfactory pyrogen-adsorbing activity.

TABLE 2

| Adsorbents and ratios of adsorption of pyrogen | |
|---|---|
| Pyrogen adsorbent | Ratio of adsorption (%) |
| Adsorbent G (P Leu-Ile) | 98 |
| Adsorbent H (Fibrous PG-OME) | 80 |
| Adsorbent I (Powdery PG-OME) | 85 |
| Adsorbent J (Surface-treated PG-OME) | 85 |

Example 13

Samples, 0.05 g (dry weight), of 6-nylon particles (mean diameter 5 μm) and 12-nylon particles (mean diameter 5 μm) both available in the market, and the adsorbent prepared in Example 9 were washed sequentially with a 10 mM pyrogen-free phosphate buffer of pH 7.5 (containing 1.0 M NaCl) and a 10 mM pyrogen-free phosphate buffer of pH 7.5 (containing 0.07 M of NaCl).

These samples were each brought into contact with 1 to 2 ml of a phosphate buffer (pH 7.2) having 5 mg of bovine serum albumin dissolved therein. The supernatants consequently formed were tested for the residual pyrogen content. The ratio of adsorption was found in the same manner as in Example 10.

The results were as shown in Table 3. These adsorbents invariably showed highly satisfactory pyrogen-adsorbing activity. The ratios of recovery of bovine serum albumin were in the range of 75 to 90%.

TABLE 3

| Adsorbents and ratios of adsorption of pyrogen | |
|---|---|
| Pyrogen adsorbent | Ratio of as adsorption (%) |
| 6-Nylon | 85 |
| 12-Nylon | 95 |
| Adsorbent K (Paa) | 85 |

Example 14

A mixture of 0.025 g (dry weight) of 6-nylon particles (mean diameter 5 μm) and 0.025 g (dry weight) of 12-nylon particles (mean diameter 5 μm) both available in the market was treated in the same manner as in Example 13 and tested for the amount of pyrogens. The ratio of adsorption was found in the same manner as in Example 10.

As the result, the ratio of adsorption of pyrogens was found to be 88%.

The detection of pyrogens was accomplished by the use of a toxinometer (produced by Wako Pure Chemical Industries Ltd.).

It is noted from the foregoing, particularly from the examples, that the pyrogen adsorbents of the present invention were invariably effective in removing pyrogens with very high selectivity without lowering the ratio of recovery of the medicinal substance subjected to purification.

The adsorbents were prepared very easily. Thus, they constitute themselves highly satisfactory adsorbents applicable for commercial production of pharmaceutical goods.

What is claimed is:

1. A water-insoluble pyrogen-adsorbent comprising an amino acid homopolymer containing acidic side chains or an amino acid copolymer containing acidic side chains wherein all of the side chain carboxyl groups are in the form of an amide with a polyamine selected from the group consisting of alkyl and aralkyl amines containing at least two amine groups of pKa not less than 6.5; or wherein a pyrogen adsorbing effective amount of the side chain carboxyl groups are in the form of an amide with said polyamine and the others are in the form of an ester with an alkyl or aralkyl alcohol; excluding polyglutamic acid derivatives wherein the side chain carboxyl groups are amidated with ethylene diamine and modified with glutaric acid via said ethylene diamine.

2. The pyrogen adsorbent of claim 1, wherein said amino acid homopolymer or copolymer is immobilized on a porous water-insoluble carrier.

3. A method for reducing the pyrogen content of a pyrogen-containing solution by contacting the solution with a water-insoluble pyrogen-adsorbent material comprising an amino acid homopolymer containing acidic side chains or an amino acid copolymer containing acidic side chains wherein all of the side chain carboxyl groups are in the form of an amide with a polyamine selected from the group consisting of alkyl and aralkyl amines containing at least two amine groups of pKa not less than 6.5; or wherein a pyrogen adsorbing effective amount of the side chain carboxyl groups are in the form of an amide with said polyamine and the others are in the form of an ester with an alkyl or aralkyl alcohol; excluding polygutamic acid derivatives wherein the side chain carboxyl groups are amidated with ethylene diamine and modified with glutaric acid via said ethylene diamine.

4. The method according to claim 3, wherein said amino acid homopolymer or copolymer is immobilized on a porous water-insoluble carrier.

* * * * *

UNITED STATES PATENT AND TRADEMARK OFFICE
CERTIFICATE OF CORRECTION

PATENT NO. : 5,279,821
DATED      : January 18, 1994
INVENTOR(S): Chuichi Hirayama et al.

It is certified that error appears in the above-indentified patent and that said Letters Patent is hereby corrected as shown below:

On the title page, Item [75],

The inventor's information should read:

--Chuichi Hirayama; Hirotaka Ihara; Shunsei Tsunoda, all of Kumamoto; Katsutoshi Aihara, Ueki; Kazufumi Yagyu; Masao Honma, both of Kawasaki, all of Japan--

Signed and Sealed this

Twenty-first Day of March, 1995

Attest:

BRUCE LEHMAN

*Attesting Officer*     *Commissioner of Patents and Trademarks*